(12) United States Patent
Tanaka et al.

(10) Patent No.: US 9,714,408 B2
(45) Date of Patent: Jul. 25, 2017

(54) CELL CULTURE METHOD

(75) Inventors: Satoshi Tanaka, Yokohama (JP); Yoichi Ishizaki, Yokohama (JP); Ryo Suenaga, Yokohama (JP); Yoriko Tokita, Kanagawa (JP); Masahito Kogure, Kanagawa (JP)

(73) Assignee: Toyo Seikan Group Holdings, LTD., Tokyo (JP)

( * ) Notice: Subject to any disclaimer, the term of this patent is extended or adjusted under 35 U.S.C. 154(b) by 1145 days.

(21) Appl. No.: 12/450,480

(22) PCT Filed: Apr. 24, 2008

(86) PCT No.: PCT/JP2008/057900
§ 371 (c)(1),
(2), (4) Date: Sep. 28, 2009

(87) PCT Pub. No.: WO2008/136339
PCT Pub. Date: Nov. 13, 2008

(65) Prior Publication Data
US 2010/0062530 A1 Mar. 11, 2010

(30) Foreign Application Priority Data
Apr. 27, 2007 (JP) ................. 2007-119113

(51) Int. Cl.
*C12N 5/02* (2006.01)
*C12M 1/34* (2006.01)
*C12M 1/00* (2006.01)
*C12M 1/06* (2006.01)
*C12M 1/26* (2006.01)

(52) U.S. Cl.
CPC ............ *C12M 41/32* (2013.01); *C12M 23/14* (2013.01); *C12M 23/26* (2013.01); *C12M 27/02* (2013.01); *C12M 29/26* (2013.01); *C12M 33/18* (2013.01); *C12M 41/26* (2013.01); *C12M 41/44* (2013.01)

(58) Field of Classification Search
None
See application file for complete search history.

(56) References Cited

U.S. PATENT DOCUMENTS

| 5,002,890 A | * | 3/1991 | Morrison | 435/297.3 |
| 5,017,490 A | | 5/1991 | Taiariol et al. | |
| 5,026,650 A | * | 6/1991 | Schwarz | C12M 23/24 |
| | | | | 261/83 |
| 5,126,238 A | | 6/1992 | Gebhard et al. | |
| 5,316,905 A | * | 5/1994 | Mori et al. | 435/3 |
| 6,080,581 A | * | 6/2000 | Anderson | C12M 27/10 |
| | | | | 435/394 |
| 2007/0037276 A1 | | 2/2007 | De Crecy | |

FOREIGN PATENT DOCUMENTS

| JP | EP0263634 | * | 4/1988 | ............ C12M 1/00 |
| JP | 63192374 | | 8/1988 | |
| JP | 2000-125848 A | | 5/2000 | |
| JP | 2002-255277 A | | 9/2002 | |
| JP | 2004-89136 A | | 3/2004 | |
| JP | 2004-323077 A | | 11/2004 | |
| NL | WO2007001173 | * | 1/2007 | ............ C12M 1/02 |

OTHER PUBLICATIONS

Ham et al. "Media and Growth Requirements" Methods in Enzymology: Cell Culture v58, 1979, Chapter 5, p. 44-93.*
Oller et al. "Growth of mammalian cells at high oxygen concentrations" Journal of Cell Science 94, 43-49 (1989).*
Dictionary.com, "closed system," in The American Heritage® Science Dictionary © 2002. Source location: Houghton Mifflin Company. http://dictionary.reference.com/browse/closed system. Available: http://dictionary.reference.com. Accessed: Jun. 3, 2015.*
Bibila et al. "Monoclonal Antibody Process Development Using Medium Concentrates" Biotechnol. hog. 1994, 10, 87-96.*
NASA Tech Brief "RegulaUng Glucose and pH, and Monitoring Oxygen in a Bloreactcr" Aug. 1, 2006, 2pgs.*
European Patent Office, "Extended European Search Report for EP 08 75 1999", May 14, 2013, 7 pgs.
Office Action issued in corresponding European Application No. 08751999.7, mailed Mar. 11, 2015 (5 pages).

* cited by examiner

*Primary Examiner* — Thane Underahl
(74) *Attorney, Agent, or Firm* — Osha Liang LLP

(57) ABSTRACT

In a cell culture in a sealed cell culture container, gradual deterioration of culture environment is prevented. A cell culture method in which cell culture is conducted by adding a fresh culture medium to a culture container in which cells and a culture medium are enclosed, which includes the steps of adjusting the pH of said culture medium to be added to be higher than the pH which is optimum for culture of the cells, and/or adjusting the partial pressure of dissolved carbon dioxide of the culture medium to be added to be lower than the pressure which is optimum for culture of the cells, and/or adjusting the partial pressure of dissolved oxygen of the culture medium to be added to be higher than the pressure which is optimum for culture of the cells; and mixing the adjusted culture medium and the culture medium in said culture-container to adjust at least any of the pH, the partial pressure of dissolved carbon dioxide and the partial pressure of dissolved oxygen to be optimum for culture of said cells, thereby to culture the cells in the culture container.

19 Claims, 3 Drawing Sheets

1: Cell culture system

1: Cell culture system

CELL CULTURE METHOD

TECHNICAL FIELD

The present invention relates to a cell culture method in which the amount of dissolved gases and the pH of a culture medium to be added are adjusted such that an optimum culture environment can be maintained.

BACKGROUND ART

In recent years, a cell culture technology has been developed in which cells, tissues, microorganisms or the like are cultured under an artificial environment, and has been actively used in the medical fields including the production of biological medicines, the gene therapy or regenerative medical therapy and the immuno-cell therapy.

This cell culture technology has already been put into practice in a number of applications where a large amount of cells are required to be cultured efficiently, such as the production of monoclonal antibodies or the regeneration of a skin, and has become a technology of crucial importance.

Under such circumstances, with an aim of culturing efficiently a large amount of cells, various cell culture apparatuses have heretofore been proposed.

For example, the cell culture equipment disclosed in Patent Document 1 has a configuration in which a container main body is provided with a cell culture bag and a prohibiting member for prohibiting the circulation of a culture medium in the culture bag. In this technology, the culture region is divided by means of this prohibiting member, thus enabling gradual extension of the culture region with the proliferation of cells.

By using such cell culture equipment, culture can be conducted continuously within the same culture bag from start to end.

The equipment for in-vitro proliferation disclosed in Patent Document 2 is provided with a series of culture sub-compartments each having a culture space and a regulating means which variably permits or precludes medium intercommunication between sub-compartments, in which a culture region is gradually extended with the proliferation of cells.

With this technology, a sufficiently small-scale starting environment for ensuring viability of the cells, and an enlarging environment can be provided, whereby a high cell number cell masses can be cultured without the risk of transfer contamination economically while saving time.

The culture apparatus disclosed in Patent Document 3 is a culture apparatus for culturing cells which grow along the bottom surface thereof, in which the bottom surface area can be enlarged with the growth of cells.

Therefore, by this technology, cells can be proliferated efficiently in a single container.

However, in these conventional cell culture apparatuses, no special contrivance is made on a culture medium which is to be added when the culture region is extended.

For example, Patent Document 1 states that, if cells proliferate to a desired number in a culture region partitioned by a first prohibiting member, the bag is then partitioned by means of a second partitioning member, and the amount of a culture medium is determined according to the proliferation capability of cells being cultured such that the cell density can be maintained at an appropriate level when the culture region is extended. Patent Document 1 states that the amount of a culture medium is generally determined such that the cell density at the time of starting culture or at the time of extending a culture region becomes about $1\times10^5$/ml, and that the cell density may be appropriately determined in accordance with the type of cells used, the characteristics of proliferation or the purpose of culture.

In Patent Document 1, no clear statement is made on how to adjust the components of a culture medium to be added. Therefore, it appears that an optimum culture medium which is used in the original culture medium is added.

However, the culture environment is gradually deteriorated with the proliferation of cells. Therefore, when a culture medium which is the same as the original culture medium is added, although the culture environment is improved immediately after the addition, it is impossible to maintain the environment of the original culture medium.

That is, as a result of cell proliferation, the amount of dissolved oxygen in a culture medium is decreased and the amount of dissolved carbon dioxide in a culture medium is increased. In addition, the pH of the culture medium is gradually decreased by the generation of lactic acid or for other reasons. If a culture medium having the same conditions as those of the original culture medium is added to such a culture medium in the same quantity, for example, it is impossible to allow the entire culture medium to recover the initial optimum environment.

Such a problem also occurs when implementing the inventions disclosed in Patent Documents 2 and 3.

Patent Document 1 states that a bag is put in a carbon dioxide gas culture apparatus, the bag is allowed to stand in a gas atmosphere which is required for the culture, and the conditions such as culture temperature, culture time, pH and carbon dioxide concentration are set in accordance with the type of cells to be used.

Patent Document 2 states that, when the cell growth and viability reaches its limit in the first sub-compartment, the contents thereof (cells, medium) are transferred to the next serial sub-compartment, and, in the next sub-compartment, the cell mass from the first sub-compartment is provided with the conditions required for a further increase with viability being retained according to the culture medium added therein, the volume, or the like.

Furthermore, Patent Document 3 states that, by maintaining menchymal stem cells and a culture medium, which have been mixed, at culture conditions such as a predetermined temperature and a carbon dioxide concentration, cells are subject to secondary culture for a prescribed period of time under fixed culture conditions.

In these conventional technologies, as mentioned above, no consideration is made on component conditions of a culture medium to be added, and a culture medium having the same conditions as those of the original medium is added, and culture conditions such as temperature and $CO_2$ concentration are adjusted after the addition.

Patent Document 1: JP-A-2000-125848
Patent Document 2: Japanese Patent No. 2981684
Patent Document 3: JP-A-2004-89136

DISCLOSURE OF THE INVENTION

Problems to be Solved by the Invention

However, actually, an environment which has been once deteriorated by cell proliferation cannot be improved appropriately only by these methods. The pH, the amount of dissolved carbon dioxide, the amount of dissolved oxygen or the like cannot be constantly maintained at an optimum level.

Among other related art documents, no document is found in which a statement is made on a technology capable of maintaining the culture environment in cell culture in a sealed culture container at an optimum level.

The present invention has been made in view of the above-mentioned circumstances, and an object thereof is to provide a cell culture method, a cell culture system and a culture medium adjustment apparatus which, in cell culture using a sealed culture container, can maintain cell culture environment at an optimum level after a fresh culture medium is added to and mixed with a culture medium during culture by adjusting in advance the pH and the amount of dissolved gases of the culture medium to be added.

Means for Solving the Problem

In order to attain the above-mentioned object, the cell culture method of the present invention is a cell culture method in which a fresh culture medium is added to a culture container where cells and a culture medium are enclosed to culture said cells, comprising the steps of: adjusting the pH and the amount of dissolved gases of the fresh culture medium to be added; and mixing the adjusted culture medium and the culture medium in said culture apparatus such that the condition of the culture medium in the culture container can be optimum for culture of said cells, thereby to culture said cells in the culture container.

According to this cell culture method, in adding a fresh culture medium to a culture medium in a culture container, it is possible to adjust a culture medium to be added such that the condition of a culture medium after mixture can be optimized.

Conventionally, even if a fresh culture medium is added, a culture medium after the addition cannot be optimized, and culture environment is gradually deteriorated to prevent cells from being proliferated. According to the present invention, since a culture medium after the addition of a fresh medium can be optimized, the culture environment can always be maintained at an optimum condition.

The cell culture method of the present invention comprises the steps of:
adjusting the pH of the culture medium to be added to be higher than the pH which is optimum for culture of said cells, and/or adjusting the partial pressure of dissolved carbon dioxide of the culture medium to be added to be lower than the pressure which is optimum for culture of the cells, and/or adjusting the partial pressure of dissolved oxygen of the culture medium to be added to be higher than the pressure which is optimum for culture of the cells; and mixing the adjusted culture medium and the culture medium in the culture container to adjust at least any of the pH, the partial pressure of dissolved carbon dioxide and the partial pressure of dissolved oxygen to be optimum for culture of the cells, thereby to culture said cells in the culture container.

Due to such a cell culture method, it is possible to adjust the pH, the partial pressure of dissolved carbon dioxide and the partial pressure of dissolved oxygen of a culture medium to be added are respectively adjusted to a value exceeding an optimum value for cell culture, i.e., in a direction opposite to the direction in which each value changes by culture to exceed the optimum value. The thus adjusted culture medium can be mixed with the culture medium in the cell culture apparatus.

Therefore, the condition of a culture medium after mixing can be restored to a condition optimum for cell culture, whereby the culture environment can always be maintained at an optimum level.

The cell culture medium of the present invention is a method wherein the volume of the culture container is expanded to allow the fresh culture medium to be added.

Due to such a cell culture method, it is possible to extend the sealed culture container so as to increase the culture volume by various techniques, whereby, when a fresh culture medium is added, a culture environment after the addition of the fresh culture medium can be maintained at an optimum level.

The cell culture method of the present invention is a method wherein the culture container is made of a soft packing material, and the culture container is pressed by means of a predetermined member so as to divide the culture container into two or more chambers including a culture part and an extensible part, and the member and the culture container are moved relatively in accordance with an increase in number of cells in the culture part, whereby the volume of the culture part is increased.

Due to such a cell culture method, by using a soft packing material in the culture container, and by dividing the culture container into a culture part and an extensible part by using a roller member, for example, the culture part can be extended with an increase in the number of cells being cultured, and, when a culture medium is added when extending the culture part, a fresh culture medium can be added such that a culture medium after the mixing can be optimum.

Therefore, the culture medium is not deteriorated even though the number of cells being cultured is increased, and the culture environment can be constantly maintained at an optimum level.

Furthermore, in the cell culture method of the present invention, the pH of the culture medium in the culture container after the mixing is 6.5 to 7.5.

In the cell culture method of the present invention, the partial pressure of dissolved carbon dioxide of a culture medium in the culture container after the mixing is 20 mmHg to 50 mmHg.

In the cell culture method of the present invention, the partial pressure of dissolved oxygen of a culture medium in the culture container after the mixing is 115 mmHg to 170 mmHg.

In the cell culture method of the present invention, the pH, the partial pressure of dissolved carbon dioxide and the partial pressure of dissolved oxygen of a culture medium after a fresh culture medium is added can be optimized respectively, whereby the cell culture environment can always be maintained at an optimum level.

In the cell culture method of the present invention, the cell density of the culture container after mixing is $5 \times 10^3$/ml to $3 \times 10^6$/ml.

Due to such a cell culture method, the cell density after addition of a new culture medium can be optimum, i.e., not too low and not too high.

Therefore, cell proliferation efficiency can be maintained at an optimum level.

In addition, the cell culture system of the present invention is a cell culture system in which a fresh culture medium is added to a culture container in which cells and a culture medium are enclosed, wherein the cell culture system is provided with a culture medium adjusting apparatus which adjusts the pH and the amount of a dissolved gas of the culture medium to be added, a culture container in which a culture medium and cells are enclosed, and a tube which supplies the culture medium to be added from the culture medium adjustment apparatus to said culture container.

Due to such a configuration of a cell culture system, a culture medium to be added to a culture container in which a culture medium and cells are enclosed can be adjusted such that the condition of a culture medium after mixing can be optimum.

Accordingly, the culture environment can be constantly maintained at an optimum level.

The cell culture system of the present invention further comprises a cell culture apparatus in which the culture container made of a soft packing material is pressed by means of a predetermined member so as to divide the culture container into two or more chambers including a culture part and an extensible part, the member and the culture container are allowed to move relatively in accordance with an increase in number of cells in the culture part, whereby the volume of the culture part is increased.

This cell culture system is provided with a cell culture apparatus which divides the culture container into a culture part and an extensible part and increases the volume of the culture part according to an increase in the number of cells. Therefore, when the volume of the culture part is increased, a fresh culture medium is required to be added.

According to the present invention, the condition of a culture medium to be added can be adjusted such that the condition of a culture medium after mixing can be optimized, whereby the culture environment can constantly be maintained at an optimum level.

The culture medium adjustment apparatus of the present invention is a culture medium adjustment apparatus in which a fresh culture medium is added to a culture container in which cells and a culture medium are enclosed, wherein the pH of the culture medium to be added is adjusted to be higher than the pH which is optimum for culture of the cells, and/or the partial pressure of dissolved carbon dioxide of the culture medium to be added is adjusted to be lower than the pressure which is optimum for culture of the cells, and/or the partial pressure of dissolved oxygen of the culture medium to be added is adjusted to be higher than the pressure which is optimum for culture of the cells.

Due to such a configuration of the culture medium adjusting apparatus, when adding a fresh culture medium to a culture container in which cells and a culture medium are enclosed, the culture medium to be added can be adjusted such that the condition of a culture medium after the addition is optimized.

Advantageous Effects of the Invention

According to the present invention, when a fresh culture medium is added to a culture medium in a culture container, the culture medium to be added can be adjusted such that the condition of the culture medium after mixing can be optimum.

Accordingly, it is possible to optimize the culture medium after mixing, and the culture environment can constantly be maintained at an optimum level.

BEST MODE FOR CARRYING OUT THE INVENTION

Preferred embodiments of the cell culture method, the cell culture system and the culture medium adjustment apparatus of the present invention will be explained hereinbelow with reference to the drawings.

First Embodiment

Figure 1:
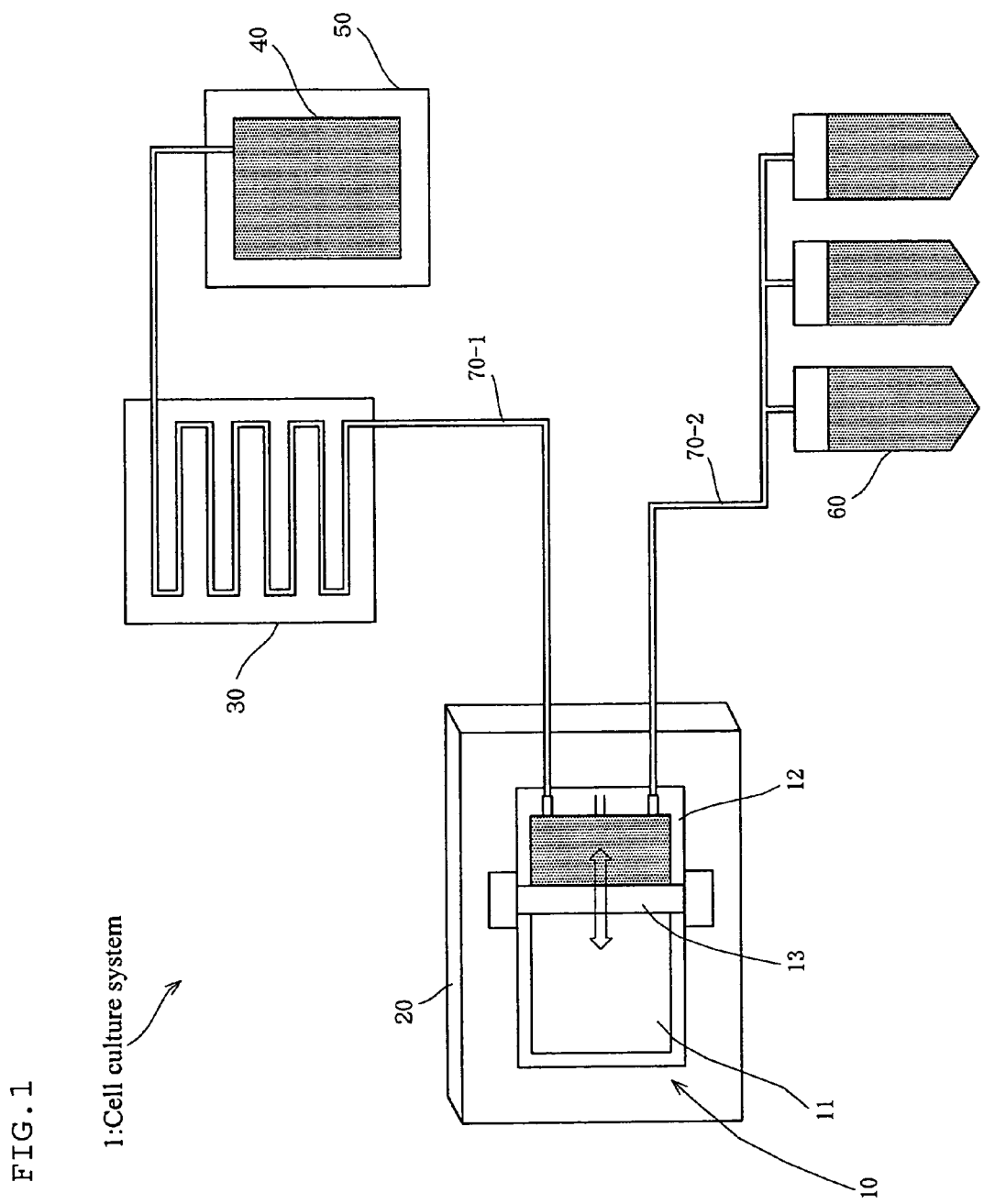
FIG. 1 is a block diagram showing a configuration of the cell culture system according to a first embodiment of the present invention.
Figure 2:
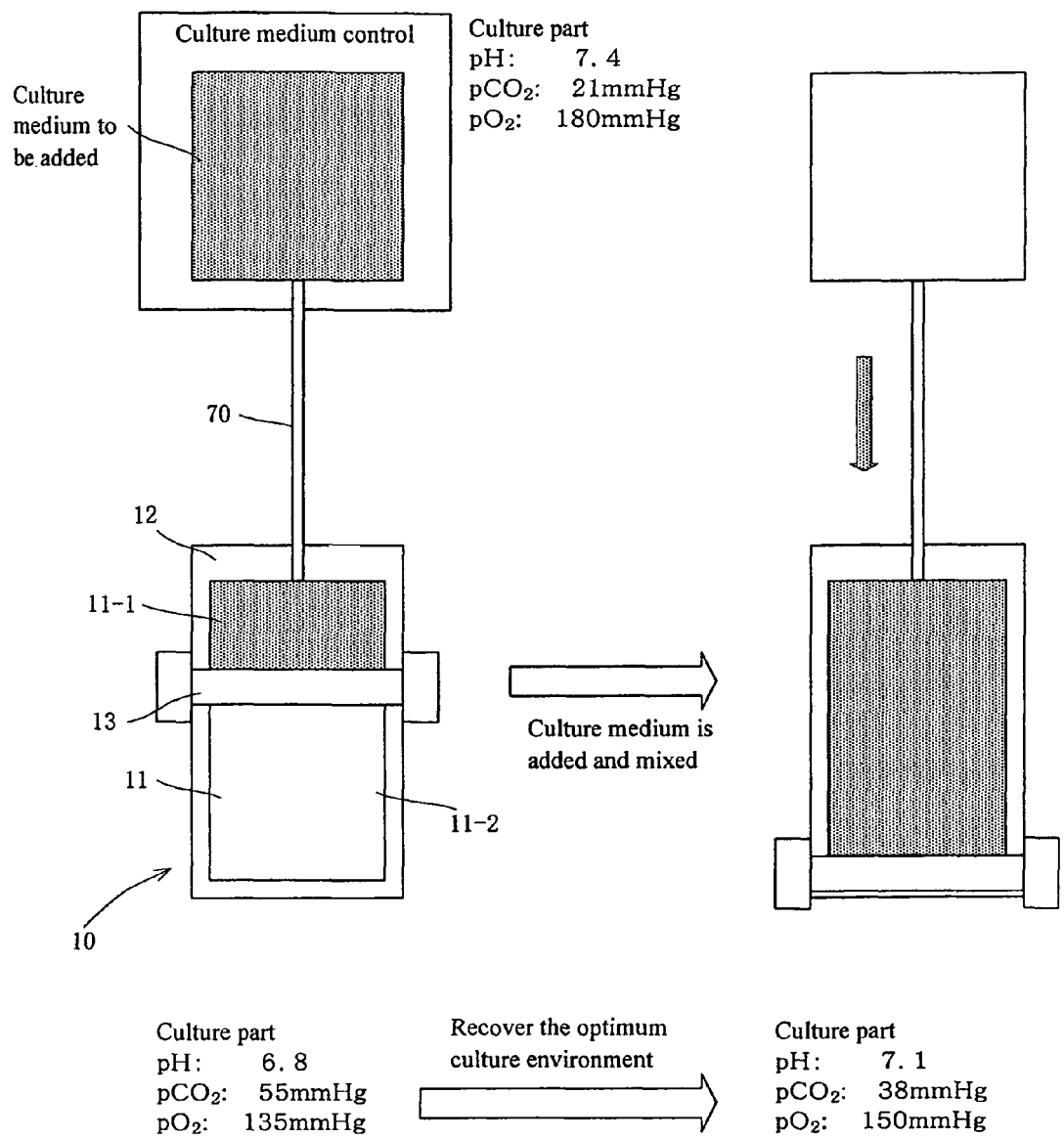
FIG. 2 is a view showing the environment of the culture part before and after the addition of a culture medium in the cell culture system according to a first embodiment of the present invention.

The configuration according to the first embodiment of the present invention will be explained with reference to FIG. 1. FIG. 1 is a block diagram showing the configuration of the cell culture system of this embodiment.

As shown in FIG. 1, the cell culture system of this embodiment is provided with a cell culture apparatus 10, an incubator 20, a culture medium adjustment apparatus (culture medium adjustment apparatus) 30, a culture medium storage apparatus (culture medium storage container) 40, a storage apparatus 50, a harvest container 60 and a tube 70.

As shown in FIG. 1, the cell culture apparatus 10 is provided with a culture container 11, a container table 12 and a roller 13.

The culture container 11 is a container in which cells to be cultured (cells being cultured) or a culture medium for culturing the cells are enclosed and culture is conducted. In this culture container 11, a part capable of enclosing cells being cultured or a culture medium is referred to as a culture part 11-1 and a part in which cells being cultured or a culture medium cannot enter by the partition of the roller 13 is referred to as an extensible part 11-2.

The culture container 11 is made of a soft packing material and is formed in a bag-like shape (bag type).

The soft packing material is a packing material which imparts flexibility and softness to a packing material. Due to the use of the soft packing material, the culture container 11 can flexibly change the volume of a culture part 11-1 by the pressing and rotation of the roller 13. A soft packing material is a well-known technology which is disclosed, for example, in JP-A-2002-255277 (Food Package Using Soft Packaging Film Sheet and Food Taking-Out Method) or in JP-A-2004-323077 (Pressurized Spouting Bag-shaped Container).

In addition, the culture container 11 has gas permeability which is necessary for the culture of cells. Due to this gas permeability, it is possible to allow the cell culture system to be a closed (enclosed) system. In addition, the culture container 11 is partly or entirely transparent so that the contents thereof can be visibly confirmed.

Specific examples of the packing material satisfying the conditions as the culture container 11 include polyolefins, ethylene-vinyl acetate copolymers, styrene-based elastomers, polyester-based thermoplastic elastomers, silicone-based thermoplastic elastomers and silicone rubber.

Each of the four sides of this culture container 11 is sealed. However, two or more tubes 70 are connected to one of these sides. Of these two tubes, one is used for injecting cells being cultured or a culture medium from outside to the culture part 11-1 (tube 70-1), and the other one is used for harvesting cells being cultured or a culture medium from the culture part 11-1 (tube 70-2). When three tubes 70 are connected as shown in FIG. 1, the third tube is a sampling tube which is used for taking cells being cultured or a culture medium out of the culture part 11-1 as a sample.

Examples of the material for the tube 70 include silicone rubber, soft vinyl chloride resins, polybutadiene resins, ethylene-vinyl acetate copolymers, chlorinated polyethylene resins, polyurethane-based thermoplastic elastomers, polyester-based Thermoplastic elastomers, silicone-based thermoplastic elastomers and styrene-based elastomers, such as SBS (styrene-butadiene-styrene), SIS (styrene-isoprene-styrene), SEBS (styrene-ethylene-butylene-styrene) and SEPS (styrene-ethylene-propylene-styrene). These are improved in gas permeability.

The container table 12 is a flat table in which the culture container 11 is placed on the upper surface thereof, and the roller 13 is placed on the upper surface of the culture container 11.

The roller 13 is formed to have a cylindrical shape, and arranged on the upper surface of the culture container 11 such that the axial direction thereof becomes parallel with the width direction of the culture container 11. As shown in FIG. 1, it is allowed to move by rotation horizontally along the longitudinal direction of the culture container 11.

The length in the axial direction of this roller 13 is longer than the width of the culture container 11. In addition, the roller 13 is a mechanism in which the surface of the roller 13 pushes the culture container 11 by the self weight or the like.

Due to such a configuration, the culture container 11 is divided into two chambers, i.e. the culture part 11-1 and the extensible part 11-2, with a portion which is pressed by the roller 13 being a boundary. In this case, a part provided on the side to which the tube 70 is attached serves as the culture part 11-1, in which cells being cultured or a culture medium are enclosed.

Meanwhile, in the cell culture apparatus 10, two or more rollers 13 may be provided and two or more culture parts 11-1 and two or more extensible parts 11-2 may be provided, respectively for example. Specifically, chambers provided on the both end sides of the longitudinal direction of the culture container 11 are allowed to be a culture part 11-1A and a culture part 11-1B, respectively, and a chamber formed in the center is allowed to be the extensible part 11-2.

When the roller 13 moves by rotation in the longitudinal direction of the culture container 11 while being in contact with the upper surface of the container, the volume of the culture part 11-1 is allowed to change continuously.

Specifically, when the cells are being cultured in the culture part 11-1, the roller 13 is controlled so as to move in a direction in which the volume of the culture part 11-1 is increased. As a result, the volume of the culture part 11-1 can be kept at an optimum level according to the culture status.

On the other hand, when a culture medium or cells being cultured are harvested after the completion of the culture, the roller 13 moves in a direction in which the volume of the culture part 11-1 is reduced. As a result, a culture medium or cells being cultured which have been pressed by means of the roller 13 are pushed outside (for example, in a harvest container 60 (mentioned later)) through the tube 70, whereby they can be automatically harvested.

An incubator 20 has a configuration in which the cell culture apparatus 10 is accommodated in the inside thereof, whereby the temperature, the oxygen concentration and the carbon dioxide concentration of the culture part 11-1 can be controlled to ensure a stable culture environment.

The cell culture apparatus 30 heats a culture medium in a culture medium storage container 40 which is kept cool in a storage apparatus 50 to a temperature suitable for cell culture through a tube 70-1, and controls the pH, the partial pressure of dissolved carbon dioxide and the partial pressure of dissolved oxygen of a culture medium.

In this case, the culture medium adjustment apparatus 30 adjusts the pH of a culture medium to a value higher than a pH value which is optimum for cell culture such that, after mixing with a culture medium in the culture container, the culture medium has an optimum pH value.

In addition, the cell culture apparatus 30 adjusts the partial pressure of dissolved carbon dioxide to a value lower than a partial pressure of dissolved carbon dioxide which is optimum for cell culture such that, after mixing with a culture medium in the culture container, the culture medium has an optimum partial pressure of dissolved carbon dioxide.

The culture medium adjustment apparatus 30 adjusts the partial pressure of dissolved oxygen to a value higher than a partial pressure of dissolved oxygen which is optimum for cell culture such that, after mixing with a culture medium in the culture container, the culture medium has an optimum partial pressure of dissolved oxygen.

As mentioned above, due to such a configuration of the culture medium adjustment apparatus 30, it is possible to prevent the temperature of a culture medium in the culture part 11-1 from lowering after mixing a culture medium in the culture medium storage container 40 with a culture medium in the culture container.

In addition, the pH, the partial pressure of dissolved carbon dioxide and the partial pressure of dissolved oxygen of a culture medium in the culture part 11-1 can be kept at optimum conditions.

Meanwhile, it is also possible to limit the mechanism of the culture medium adjustment apparatus 30 such that at least one of pH, partial pressure of dissolved carbon dioxide and partial pressure of dissolved oxygen is adjusted.

The culture medium storage apparatus (culture medium tank) 40 is an apparatus for keeping a culture medium to be added for injecting the culture container 11. This culture medium storage container 40 is accommodated within the storage apparatus (cooler) 50.

This culture medium storage apparatus 40 and the culture container 11 (placed on the container table 12) are connected by means of a flexible tube 70-1. This tube supplies a culture medium from the culture medium storage apparatus 40 to the culture container 11 when the culture volume is expanded.

The harvest container (a bottle for centrifugation) 60 is a container for putting cells being cultured or a culture medium which have been harvested from the culture container 11.

This harvest container 60 can be attached to a centrifugal separator, whereby cells being cultured can be harvested from a culture medium by centrifugation.

The harvest container 60 and the culture container 11 (placed on the container table 12) may be connected by means of a flexible tube 70-2. A culture medium and cells being cultured are harvested from the culture container 11 to the harvest container 60 through this tube 70-2.

Next, operation of the cell culture system (cell culture method) in this embodiment will be explained with reference to FIG. 1. The cell culture method of the present invention is not limited to the following specific operation.

First, in the cell culture apparatus 10, the volume of the culture part 11-1 of the culture container 11 is adjusted to a size which is suited to intended culture by the rotational movement of a roller. Then, in this culture part 11-1, a group of cells having a cell density higher than a certain level suitable for culture and a culture medium which is optimum for culturing them are enclosed.

Then, the temperature, carbon dioxide concentration and oxygen concentration of the incubator 20 are adjusted to values suited to culture.

A culture medium to be added to the culture container 11 is injected to the culture medium storage container 40, and the culture medium storage container 40 is kept cool in the storage apparatus 50.

Next, when cells in the culture container 11 proliferate, the roller 13 is allowed to move in accordance with the amount or density of proliferated cells to expand the volume of the culture part 11-1, and the roller 13 is arranged at an appropriate position.

Further, a culture medium to be added to the culture container 11 is supplied through the tube 70-1 from the culture medium storage apparatus 40 to the culture medium adjustment apparatus 30. At this time, a culture medium in an amount suited to the volume of the culture container 11 which is expanded by the movement of the roller 13 is supplied to the culture medium adjustment apparatus 30.

Then, by means of the culture medium adjustment apparatus 30, the pH of the culture medium in the tube 70-1 is adjusted to be optimum for cell culture after mixing the culture medium in the culture container 11 with the culture medium in the tube 70-1. Although the optimum pH varies according to cells to be cultured, it is preferred that the optimum pH be 6.5 to 7.5 in the case where various tissue cells of a human being are cultured.

As for specific means for adjusting pH, the culture medium adjustment apparatus 30 has a shape capable of adjusting the partial oxygen pressure, partial carbon dioxide pressure and temperature within the apparatus. The culture medium adjustment apparatus may have a shape capable of accommodating the tube 70-1 in its inside.

By allowing the partial pressure of dissolved carbon dioxide in the adjustment apparatus 30 to change, it is possible to adjust the pH of a culture medium in the tube 70-1. As for other pH adjustment methods, a carbonate or the like can be added to a culture medium.

Then, by means of the culture medium adjustment apparatus 30, the partial pressure of dissolved carbon dioxide of the culture medium in the tube 70-1 is adjusted to be optimum for cell culture after mixing the culture medium in the culture container 11 with the culture medium in the tube 70-1. Although the optimum partial pressure of carbon dioxide varies according to cells to be cultured, it is preferred that the optimum partial pressure of carbon dioxide be 20 mmHg to 50 mmHg in the case of a variety of tissue cells of a human being are cultured.

As for specific means for adjusting the partial pressure of dissolved carbon dioxide, by using an apparatus similar to the above-mentioned pH adjustment means and by adjusting the partial pressure of dissolved carbon dioxide within the apparatus, a culture medium in the tube 70-1 can be adjusted to have a predetermined partial pressure of dissolved carbon dioxide.

Then, by means of the culture medium adjustment apparatus 30, the partial pressure of dissolved oxygen of the culture medium in the tube 70-1 is adjusted to be optimum for cell culture after mixing the culture medium in the culture container 11 with the culture medium in the tube 70-1. Although the optimum partial pressure of dissolved oxygen after mixing varies according to cells to be cultured, it is preferred that the optimum partial pressure of dissolved oxygen be 115 mmHg to 170 mmHg in the case of various tissue cells of a human being are cultured.

As for specific means for adjusting the partial pressure of dissolved oxygen, for example, in the above-mentioned culture medium adjustment apparatus 30, the partial pressure of oxygen within the apparatus is adjusted to allow the culture medium in the tube 70-1 to have a predetermined partial pressure of dissolved oxygen.

The culture medium which has been thus adjusted by the culture medium adjustment apparatus 30 is injected through the tube 70-1 to the culture part 11-1 of the culture container 11, and mixed with the culture medium in the culture part 11-1.

As a result, the pH, partial pressure of dissolved carbon dioxide and partial pressure of dissolved oxygen of the culture medium in the culture part 11-1 after mixing can be recovered to a level optimum for culture.

Similarly, the roller 13 is allowed to move in accordance with the amount of proliferated cells or the passage of time. The roller 13 is moved such that the entire culture container 11 finally becomes the culture part 11-1.

During this process, the pH, partial pressure of dissolved carbon dioxide and partial pressure of dissolved oxygen in the culture part 11-1 can be maintained at a level optimum for culture.

When harvesting a culture medium or cells being cultured in the culture container 11, the roller 13 is allowed to move by rotation to a side to which the tube 70-2 is connected.

As a result, the volume of the culture part 11-1 is decreased, and a culture medium or the like are harvested to the harvest apparatus 60 through the tube 70-2.

In this embodiment, in the cell culture apparatus 10, the volume of the culture part 11-1 in the culture container 11 is changed by means of the roller 13. The present invention is, however, not limited to this, and the present invention can be applied to a case where the volume of the culture part 11-1 can be changed by various methods.

For example, the present invention can be applied to the following cases. As stated in Patent Document 1, the volume of a culture part in a culture bag is gradually varied by means of a prohibiting member for prohibiting the circulation of a culture medium. As stated in Patent Document 2, the volume of a culture space is gradually varied by connecting culture sub-compartments each having a culture space. Furthermore, as stated in Patent Document 3, culture is conducted by means of a culture apparatus of which the bottom surface area can be expanded.

As mentioned hereinabove, according to the cell culture system in this embodiment, when adding a fresh culture medium to a culture medium in a culture container, it is possible to adjust a culture medium to be added such that the pH, partial pressure of dissolved carbon dioxide and partial pressure of dissolved oxygen can be optimum.

Therefore, the culture medium after mixing can be optimized such that the culture environment can always be kept to have optimum conditions.

Second Embodiment

Figure 3:
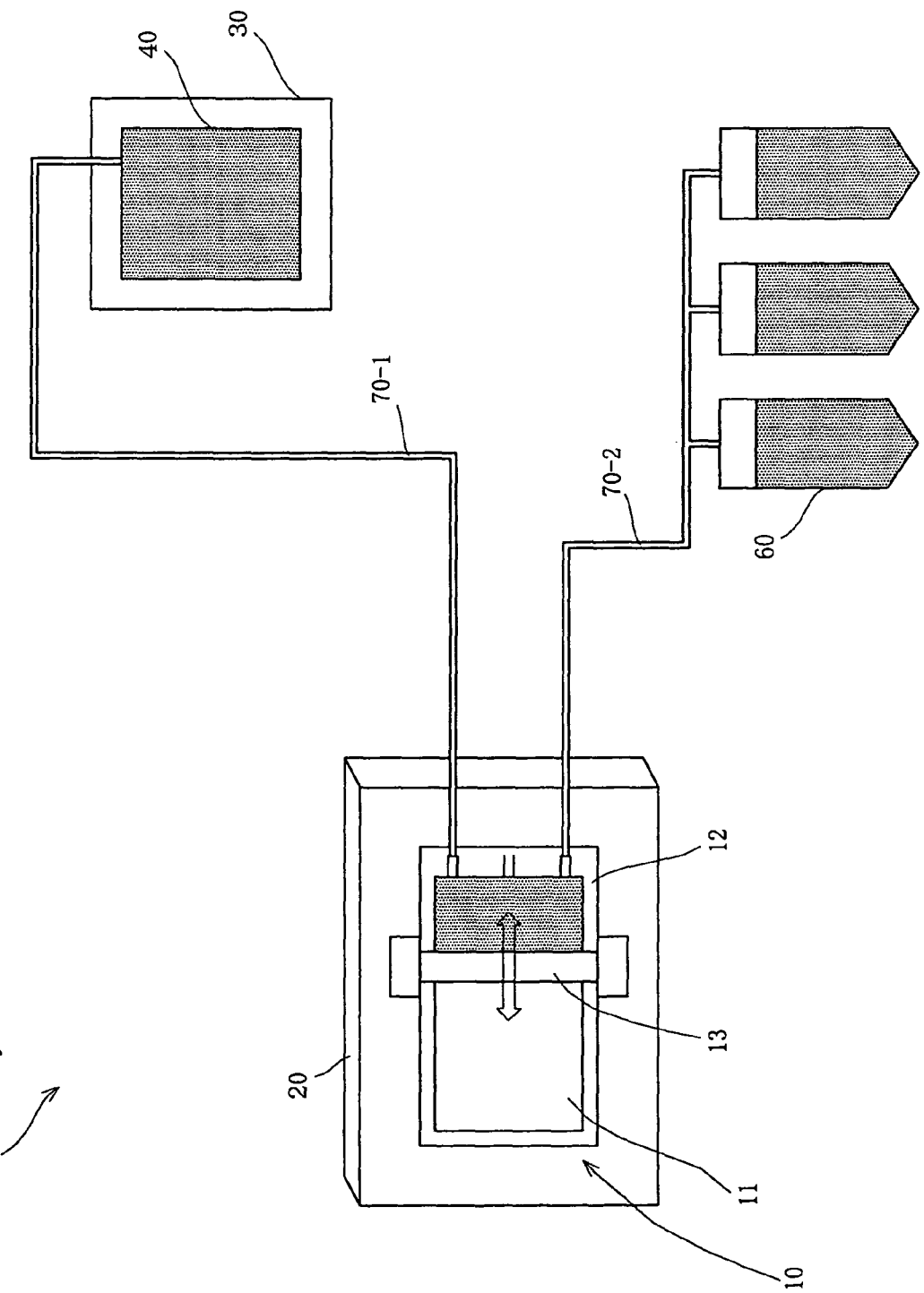
FIG. 3 is a block diagram showing a configuration of the cell culture system according to a second embodiment of the present invention.

Next, the second embodiment of the present invention will be explained with reference to FIG. 3. FIG. 3 is a block diagram showing the cell culture system of the second embodiment.

This embodiment differs from the first embodiment in that the pH, partial pressure of dissolved carbon dioxide and partial pressure of dissolved oxygen are adjusted in the culture medium storage apparatus 40. Other points are the same as those in the first embodiment.

As shown in FIG. 3, in this embodiment, the culture medium storage apparatus 40 is provided within the culture medium adjustment apparatus 30 such that the pH, partial pressure of dissolved carbon dioxide and partial pressure of dissolved oxygen in the culture medium storage apparatus 40 can be adjusted.

It is also preferred that this culture medium adjustment apparatus 30 have a cooling function so that it can be kept cool like the storage apparatus 50 in the first embodiment.

By doing this, the entire cell culture system configuration can be more simplified.

EXAMPLES

Example 1

A culture apparatus having a volume of 1 L was placed on a container table, and a roller was moved such that the volume of a culture part in the culture apparatus became 0.1 L.

Next, 0.1 L of RPMI Medium 1640 (manufactured by GIBCO Corporation) was added to the culture part as the culture medium. Then, jurkat, human T-cell leukemia cells, were injected in an amount of 10,000,000 as culture cells. The pH of this culture medium was measured by means of an i-STAT analyzer (manufactured by Abbott Corporation), and it was found to be 7.17.

The partial pressure of dissolved carbon dioxide was measured by means of an i-STAT analyzer (manufactured by Abbott Corporation), and it was found to be 39 mmHg.

The partial pressure of dissolved oxygen was measured by means of an i-STAT analyzer (manufactured by Abbott Corporation), and it was found to be 140 mmHg.

The temperature of the culture medium was 37° C.

Then, these cells were cultured for 3 days. By adjusting the temperature of the incubator, the temperature of the culture medium was kept at 37° C.

The pH, partial pressure of dissolved carbon dioxide and partial pressure of dissolved oxygen were measured in the same manner as mentioned above. As a result, it was found that they were 6.8, 55 mmHg and 135 mmHg, respectively.

Next, on the container table, the roller was moved relatively to the culture container so as to expand the volume of the culture part to 0.2 L. To the thus-expanded culture part, 0.1 L of a culture medium was injected from the culture medium storage container 40 through the culture medium adjustment apparatus 30.

At this time, in the culture medium adjustment apparatus 30, the pH, the partial pressure of dissolved carbon dioxide and the partial pressure of dissolved oxygen of a culture medium to be added were 7.4, 21 mmHg and 180 mmHg, respectively.

Then, the pH, the partial pressure of dissolved carbon dioxide and the partial pressure of dissolved oxygen of the culture part after the fresh culture medium was added and mixed were measured in the same manner as mentioned above.

As a result, it was found that they were 7.1, 38 mmHg and 150 mmHg, respectively.

Comparative Example 1

In the same manner as in Example 1, a culture container having a volume of 1 L was placed on the container table, and a roller was moved such that the volume of a culture part in the culture apparatus becomes 0.1 L.

Next, as the culture medium, 0.5 L of RPMI Medium 1640 (manufactured by GIBCO Corporation) was prepared, and 0.1 L thereof was added to the culture part as the culture medium. Then, jurkat, human T-cell leukemia cells, were injected in an amount of 10,000,000 as culture cells.

The pH of this culture medium was measured by means of an i-STAT analyzer (manufactured by Abbott Corporation), and it was found to be 7.17.

The partial pressure of dissolved carbon dioxide was measured by means of an i-STAT analyzer (manufactured by Abbott Corporation), and it was found to be 39 mmHg.

The partial pressure of dissolved oxygen was measured by means of an i-STAT analyzer (manufactured by Abbott Corporation), and it was found to be 140 mmHg.

The temperature of the culture medium was 37° C.

Then, the culture medium was cultured for 3 days. By adjusting the temperature of the incubator, the temperature of the culture medium was kept at 37° C.

The pH, partial pressure of dissolved carbon dioxide and partial pressure of dissolved oxygen of the culture medium were measured in the same manner as mentioned above. As a result, it was found that they were 6.87, 55 mmHg and 134 mmHg, respectively.

Next, on the container table, the roller was moved relatively to the culture container so as to expand the volume of the culture part to 0.2 L. To the thus-expanded culture part, 0.1 L of the culture medium (7.17, 39 mmHg, 140 mmHg) which was the same as that initially injected was injected.

The pH, partial pressure of dissolved carbon dioxide and partial pressure of dissolved oxygen of the culture part after the culture medium was added and mixed were measured by the same method as mentioned above.

As a result, it was found that they were 7.03, 46 mmHg and 136 mmHg, respectively.

As mentioned above, in Example 1 where the culture medium was added using the culture method of the present invention, the pH, the partial pressure of dissolved carbon dioxide and the partial pressure of dissolved oxygen were almost similar to those at the time of starting culture. It was confirmed that the environment optimum for culture could be maintained.

On the other hand, in Comparative Example 1 where the culture medium was added by the conventional culture method, the pH, the partial pressure of dissolved carbon dioxide and the partial pressure of dissolved oxygen after the culture part was expanded to allow the culture medium to be added were poorer than the values at the time of starting culture although these were improved to values which were more suited to culture as compared with the values immediately before the addition. It was confirmed that the culture environment was gradually deteriorated even though the culture medium was added.

The present invention is not limited to the embodiment mentioned above, and it is needless to say that various modifications are possible within the scope of the present invention.

For example, in each of the above embodiments, of the cell culture conditions, only the pH, partial pressure of dissolved carbon dioxide and partial pressure of dissolved oxygen were adjusted. The present invention can be applied to other conditions so that the optimum conditions can be kept.

INDUSTRIAL APPLICABILITY

The present invention can preferably be used in the fields of biological medicines, the gene therapy or regenerative medical therapy and the immuno-cell therapy.

The invention claimed is:

1. A method of culturing cells in a culture container containing an original culture medium, comprising:
    incubating the original culture medium and cells in the culture container to produce incubated culture medium and cultured cells;
    mixing the incubated culture medium with a new culture medium in the culture container,
    wherein
        a pH of the new culture medium is higher than the pH of the original culture medium,
        a partial pressure of dissolved carbon dioxide of the new culture medium is lower than the partial pressure of dissolved carbon dioxide of the original culture medium, and
        a partial pressure of dissolved oxygen of the new culture medium is higher than the partial pressure of dissolved oxygen of the original culture medium, and wherein
        the mixing raises the pH and the partial pressure of dissolved oxygen of the incubated culture medium and lowers the partial pressure of dissolved carbon dioxide of the incubated culture medium to optimum conditions for cell culture.

2. The method according to claim 1, wherein the volume of the culture container is expanded to mix the new culture medium and the incubated culture medium in the culture container.

3. The method according to claim 2, wherein the culture container is made of a soft packing material,
    the culture container is divided into two or more chambers including a culture chamber and an extensible chamber by a predetermined member, and
    the member and the culture container move relatively in accordance with an increase in number of cells in the culture chamber, whereby the volume of the culture chamber is increased.

4. The method according to claim 1, wherein the pH of the incubated culture medium in the culture container is adjusted to 6.5 to 7.5 by the mixing.

5. The method according to claim 1, wherein the partial pressure of dissolved carbon dioxide of the incubated culture medium in the culture container is adjusted to 20 mmHg to 50 mmHg by the mixing.

6. The method according to claim 1, wherein the partial pressure of dissolved oxygen of the incubated culture medium in the culture container is adjusted to 115 mmHg to 170 mmHg by the mixing.

7. The method according to claim 1, wherein a cell density in the culture container after the mixing is $5\times10^3$/ml to $3\times10^6$/ml.

8. The method according to claim 1, the method further comprising culturing the cells after the mixing and collecting the cultured cells in a harvest container, wherein the harvest container is connected to the culture container by a tube.

9. The method according to claim 1, wherein the new culture medium is transferred from a culture medium storage container, wherein the culture medium storage container is connected to the culture container by a tube.

10. The method according to claim 8, wherein the new culture medium is transferred from a culture medium storage container, wherein the culture medium storage container is connected to the culture container by a tube.

11. The method according to claim 1, wherein the culture container is a bag-shaped container made of a soft packing material.

12. A method of culturing cells in a cell culture system, the method comprising:
    incubating the cells in a culture medium in a culture container,
    transferring a new culture medium from a culture medium storage container to the culture container containing the culture medium and cells, wherein the culture medium storage container and the culture container are connected by a tube; and
    mixing the culture medium with the new culture medium in the culture container, wherein
        the pH of the new culture medium is higher than the pH of the culture medium in the culture container at the start of incubation,
        the partial pressure of dissolved carbon dioxide of the new culture medium is lower than a partial pressure of dissolved carbon dioxide of the culture medium in the culture container at the start of incubation, and
        the partial pressure of dissolved oxygen of the new culture medium is higher than a partial pressure of dissolved oxygen of the culture medium in the culture container at the start of incubation.

13. The method according to claim 12, the method further comprising culturing the cells after the mixing and collecting the cultured cells in a harvest container, wherein the harvest container is connected to the culture container by a tube.

14. The method according to claim 13, wherein the culture container is a bag-shaped container made of a soft packing material.

15. The method according to claim 13, wherein the pH of the culture medium in the culture container is adjusted to 6.5 to 7.5 by the mixing.

16. The method according to claim 14, wherein the partial pressure of dissolved carbon dioxide of the culture medium in the culture container is adjusted to 20 mmHg to 50 mmHg by the mixing.

17. The method according to claim 15, wherein the partial pressure of dissolved oxygen of the culture medium in the culture container is adjusted to 115 mmHg to 170 mmHg by the mixing.

18. The method according to claim 9, wherein the tube from the culture medium storage container passes through a culture medium adjustment apparatus.

19. The method according to claim 12, wherein the tube from the culture medium storage container passes through a culture medium adjustment apparatus.

* * * * *